(12) United States Patent
Bondurant et al.

(10) Patent No.: US 7,542,874 B2
(45) Date of Patent: Jun. 2, 2009

(54) 2D AND 3D DISPLAY SYSTEM AND METHOD FOR FURNACE TUBE INSPECTION

(75) Inventors: Phillip D. Bondurant, Kent, WA (US);
Robert De Lorenzo, Seattle, WA (US);
Richard D. Roberts, Seattle, WA (US)

(73) Assignee: Quest Trutec, LP, Kent, WA (US)

( * ) Notice: Subject to any disclaimer, the term of this patent is extended or adjusted under 35 U.S.C. 154(b) by 0 days.

(21) Appl. No.: 11/142,776

(22) Filed: Jun. 1, 2005

(65) Prior Publication Data

US 2005/0267703 A1  Dec. 1, 2005

Related U.S. Application Data

(60) Provisional application No. 60/576,276, filed on Jun. 1, 2004.

(51) Int. Cl.
*G06F 15/00* (2006.01)
(52) U.S. Cl. .................................. 702/183; 702/182
(58) Field of Classification Search ................. 702/183, 702/185, 33, 35, 36, 39, 40, 159, 171, 182; 128/916; 382/154; 69/29.13; 65/29.13
See application file for complete search history.

(56) References Cited

U.S. PATENT DOCUMENTS 4,893,933 A * 1/1990 Neiheisel et al. ............ 356/608
5,125,745 A * 6/1992 Neiheisel et al. ............ 356/602
6,359,434 B1 * 3/2002 Winslow et al. ............. 324/220
6,978,690 B1 * 12/2005 Van der Heide et al. ....... 73/865
2004/0006437 A1   1/2004 Lam et al.

OTHER PUBLICATIONS

Description of Furnace Tube Inspection System (FTIS™) (attached as Exhibit A) (in public use for more than one year prior to Jun. 1, 2004, the priority date of the present application).

* cited by examiner

*Primary Examiner*—Edward R Cosimano
*Assistant Examiner*—Douglas N Washburn
(74) *Attorney, Agent, or Firm*—Stinson Morrison Hecker LLP

(57) ABSTRACT

A system and method for displaying inspection data collected from a furnace is disclosed. The system comprises a storage device for storing the inspection data. The system also comprises a computer programmed to partition the inspection data at a plurality of data markers so as to correlate the inspection data to the physical geometry of the furnace. Each of the data markers identifies the location of a physical feature of the furnace (such as a bend, an external raised surface, cross-over piping, a thermal well, a weld, a flange, a schedule change and/or a diameter change). Preferably, the computer is also programmed to generate a display of the partitioned inspection data, wherein the display is a two-dimensional or three-dimensional representation of the tube segments of the furnace. This display may then be used to visually detect problem areas within the furnace. Various exemplary embodiments of the system and associated method are provided.

41 Claims, 11 Drawing Sheets
(7 of 11 Drawing Sheet(s) Filed in Color)

2D AND 3D DISPLAY SYSTEM AND METHOD FOR FURNACE TUBE INSPECTION

CROSS-REFERENCE TO RELATED APPLICATIONS

This application claims priority to U.S. Provisional Patent Application Ser. No. 60/576,276, filed Jun. 1, 2004, entitled "2D and 3D Display System and Method for Furnace Tube Inspection," which is incorporated herein by reference.

STATEMENT REGARDING FEDERALLY SPONSORED RESEARCH OR DEVELOPMENT

Not Applicable.

BACKGROUND OF THE INVENTION

1. Field of the Invention

The present invention relates generally to furnace tube inspection systems, and more particularly to a system and method for displaying inspection data in a two-dimensional and/or three-dimensional format to enable visual detection of problem areas within the furnace.

2. Description of Related Art

As depicted in FIGS. 1A-1C, a furnace is generally comprised of several hundred to several thousand feet of serpentine tubing that is characterized by straight tube segments (each of which is identified as reference numeral 10) interconnected by angled bends (each of which is identified as reference numeral 20). The bends allow tight stacking of the tube segments for maximum heat transfer and efficiency. Although not shown in FIGS. 1A-1C, medium length sections of tubing may also be used to interconnect furnace tubing located in different regions of the furnace. These sections of tubing are not part of the furnace geometry, but are employed so that an inspection tool (described below) can be operated in one pass, if possible, and thus significantly reduce plant downtime.

If the plant maintenance personnel need to repair or replace a worn section of the furnace, it is very important to accurately identify which tube segment contains the worn section and where the identified tube segment is located within the furnace. In addition, it is important to obtain information regarding hot spots in the furnace so that the plant maintenance personnel may adjust the furnace to reduce or eliminate the hot spots and thereby prolong the life of the furnace and reduce cost and future plant downtime.

In this regard, furnace tube inspection systems have been developed in which an inspection tool (identified as reference numeral 30) is flushed from a launcher (shown in FIG. 1A) through the furnace (shown in FIG. 1B) and to a receiver (shown in FIG. 1C). Typically, the inspection tool collects inspection data at pre-determined time intervals as it progresses through the furnace (although the inspection data may alternatively be collected via a position-based collection system). The inspection data includes readings of the inside radius of the furnace, readings of the wall thickness of the furnace, and the like. The collected inspection data is then extracted from the inspection tool, whereby the various readings are converted to calibrated engineering units. Finally, the converted inspection data may be examined by an engineer in order to identify thinning, bulging and other flaws within the furnace.

One problem with the furnace tube inspection systems of the prior art is that it is difficult to correlate the inspection data collected from the furnace with the physical geometry of the furnace. This is due to the fact that the inspection tool does not progress through the furnace at a constant rate. Instead, the inspection tool will often ebb and flow through the furnace and/or may become momentarily stuck at a point in the structure. Also, the inspection tool may take longer to traverse a bend in the furnace. In addition, the furnace may change in schedule size or diameter and thus retard or promote the passing of the inspection tool. For example, the furnace could change from a schedule 40 to a schedule 80 (or vice versa) and thus change the rate of passage of the inspection tool, or, the furnace could change from a 4-inch inside diameter to a 6-inch inside diameter (or vice versa) and thus change the rate of passage of the inspection tool. All of these conditions generate a correlation (i.e., mapping or scaling) problem between the collected inspection data and the precise location of the inspection tool with respect to the physical geometry of the furnace. As a result, an engineer may not be able to identify the precise locations of the worn sections and/or hot spots of the furnace.

Another problem with the furnace tube inspection systems of the prior art is that the inspection data is not displayed in a manner that readily "announces" problem areas within the furnace. Conventionally, the inspection data has been presented in a one-dimensional tabular format, which is deficient in that an engineer must peruse each line of data to determine if a potential problem has arisen. It can be appreciated that this method of examining the inspection data is time-consuming, inefficient, and does not readily permit a comparison between one section of tubing and another. As such, the engineer is not able to readily detect worn sections of the furnace, and, cannot determine if hot spots are occurring during the operation of the furnace that are common to a region of the furnace.

Recently, data visualization tools have been developed that allow a slice of the inspection data to be graphically displayed in a two-dimensional format, wherein each slice comprises inspection data collected from a short axial section (e.g., less than a foot) of the furnace. While this graphical representation of the inspection data is an improvement over the one-dimensional tabular format described above, the engineer may only view one slice of the inspection data at a time. This is a significant problem when attempting to identify overall trends in the inspection data and then apply them to the real world operation of the plant.

BRIEF SUMMARY OF THE INVENTION

The present invention is directed to a system and method for displaying inspection data collected from a furnace that comprises a plurality of tube segments connected by a plurality of bends. The system includes a storage device for storing inspection data collected by an inspection tool flushed through the furnace. Preferably, the inspection data comprises a plurality of inside radius and/or wall thickness readings collected by an array of ultrasonic transducers or by a single transducer with a rotating mirror. The storage device may also store sensor data collected by one or more auxiliary sensors, such as an axial encoder, an accelerometer, a roll encoder, a gyroscope and/or an inertial navigation system.

The system also includes a computer that may be programmed to generate a plurality of data markers in relation to the inspection data, wherein each of the data markers identifies a location of a physical feature of the furnace (such as a bend, an external raised surface, cross-over piping, a thermal well, a weld, a flange, a schedule change and/or a diameter change). In some applications, the data markers are generated based upon input from a data analyst who has analyzed a two-dimensional display of the inspection data in order to identify the locations of these physical features. In other applications, the computer automatically generates the data markers based upon an analysis of the inspection data and/or sensor data collected from the furnace.

For example, the locations of the furnace bends may be identified by detecting one or more "data clues" in the inspection data and/or sensor data collected from the furnace. Examples of these "data clues" include an increase in the variation of the wall thickness readings and/or inside radius readings within a particular time interval, a decrease in the number of wall thickness readings and/or inside radius readings within a particular time interval, and/or a change in the centering of the inspection tool (all of which are more likely to occur in the bends). Other "data clues" may be detected based upon the distance traveled by the inspection tool (which may be compared with the known geometry of the furnace to locate the bends), the acceleration of the inspection tool (which is more likely to occur in the bends), and/or the roll of the inspection tool (which is likely to occur at a faster rate in the bends).

The computer is also programmed to partition the inspection data at the data markers so as to correlate the inspection data to the appropriate tube segments of the furnace. Preferably, the computer is further programmed to generate a display of the partitioned inspection data, wherein the display is a two-dimensional or three-dimensional representation of one or more of the tube segments of the furnace. The display may be used to visually detect problem areas within the furnace so that the appropriate tube segments may be repaired or replaced by the plant maintenance personnel.

The present invention has several advantages over the prior art. For example, the invention provides a processing and display methodology that allows a large amount of inspection data to be correlated with the physical geometry of the furnace. In addition, the invention provides a convenient method for displaying the inspection data on a single page for rapid assessment of problem areas within the furnace and to facilitate the observation of trends within the inspection data. Of course, other advantages of the invention will be apparent to one skilled in the art.

BRIEF DESCRIPTION OF THE DRAWINGS

This patent application contains a plurality of drawings, some of which are executed in color. Copies of the patent application, with the color drawings, will be provided by the Patent Office upon request and payment of the necessary fee. The drawings are as follows.

DETAILED DESCRIPTION OF THE INVENTION

Figure 1A:
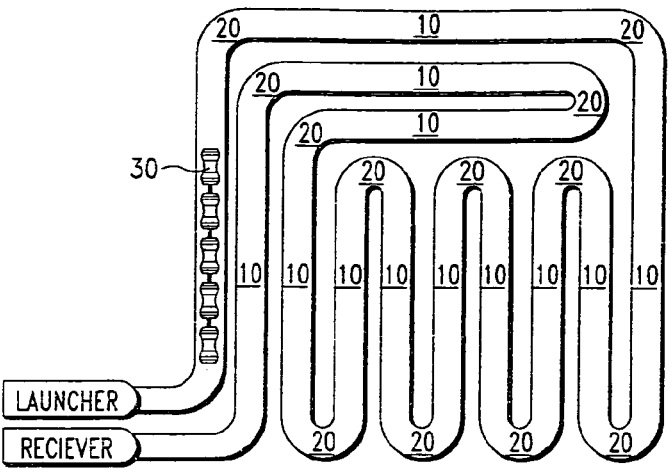
FIGS. 1A-1C are schematic diagrams of an inspection tool passing from a launcher (shown in FIG. 1A) through a furnace (shown in FIG. 1B) and to a receiver (shown in FIG. 1C)
Figure 1B:
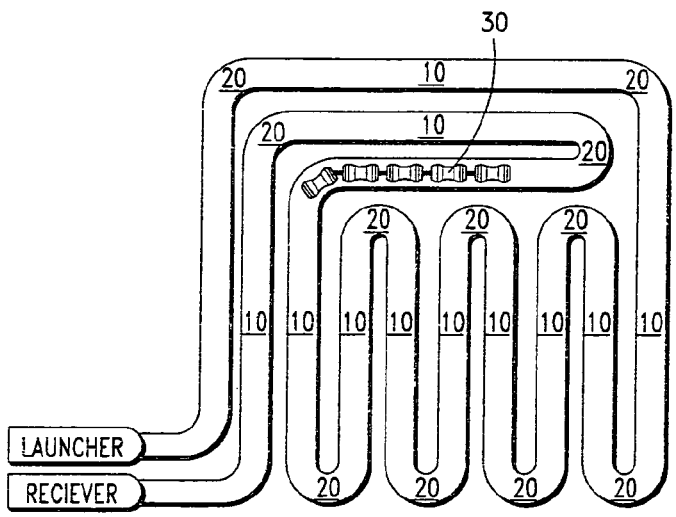
Figure 1C:
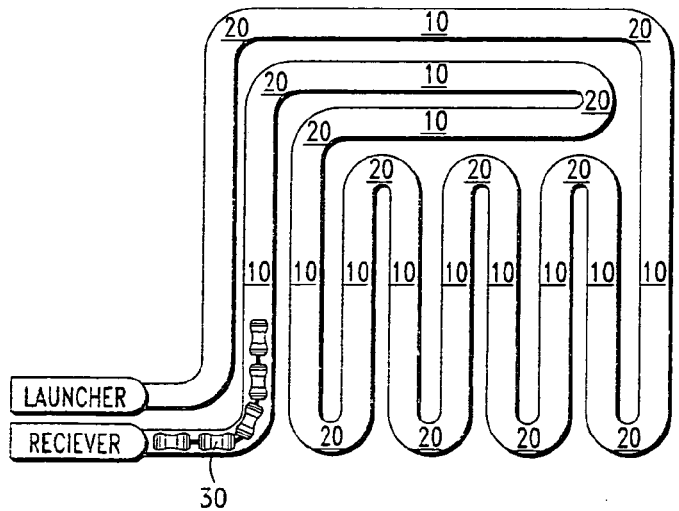

The present invention is directed to a furnace tube inspection system for a furnace that comprises a plurality of tube segments connected by a plurality of bends, such as the furnace shown in FIGS. 1A-1C. In accordance with the invention, an inspection tool is flushed through the furnace so as to collect inspection data and/or sensor data as the inspection tool progresses through the furnace. As will be described in greater detail hereinbelow, the inspection data and/or sensor data collected from the furnace may be analyzed to generate a plurality of data markers each of which identifies a physical feature of the furnace. The inspection data is then partitioned at the data markers so as to correlate the inspection data to the physical geometry (e.g., the appropriate tube segments) of the furnace. It will also be seen that the inspection data is displayed in a manner that enables the visual detection of problem areas within the furnace.

A variety of different types of physical features may be identified to assist in correlating the inspection data to the physical geometry of the furnace. Examples of such physical features include the bends of the furnace, external raised surfaces in the convection section of the furnace (e.g., fins or studs), cross-over piping, thermal wells (e.g., Weld-O-Let welded to the pipe with a threaded hole in the middle), welds between two tube segments or between a tube segment and a bend, flanges, schedule changes between two tube segments and/or diameter changes between two tube segments. While the invention will be described in detail hereinbelow with respect to the identification of the furnace bends, it should be understood that many other types of physical features may also be used to correlate the inspection data to the physical geometry of the furnace.

The inspection tool may include a variety of different devices for collecting inspection data and/or sensor data from the furnace. Preferably, the inspection tool collects the data at a predetermined time-based rate (although the inspection tool could alternatively collect the data using a position-based collection system in which data is collected when the inspection tool has progressed a predetermined distance). Using a time-based collection system, the data density is determined by the data collection rate and the speed at which the inspection tool progresses through the furnace. In a typical application, the data collection rate will range from 30 to 50 Hz per transducer, and the speed of the inspection tool will range from 1 to 2 ft/sec (although the average speed and the instantaneous speed can vary significantly in view of the fact that the inspection tool does not progress through the furnace at a constant rate). Of course, other data collection rates and tool speeds may also be used. Examples of the various types of devices that may be incorporated into the inspection tool will now be described.

Typically, one or more ultrasonic transducers are used to collect inspection data from the furnace (although a single transducer with a rotating mirror may also be used). Preferably, an array of 8, 16, 32, 64 or 128 transducers are positioned around the periphery of the inspection tool, although any number of transducers may be used. Each of the transducers is operable to measure the distance between the transducer and the inner wall of the furnace, whereby a plurality of "inside radius readings" are sequentially collected by the transducers as the inspection tool progresses through the furnace. Each of the transducers is also operable to measure the wall thickness of the furnace, whereby a plurality of "wall thickness readings" are sequentially collected by the transducers as the inspection tool progresses through the furnace. These readings may be used to detect inner surface anomalies of the furnace, such as pitting, corrosion, deformation and/or cracking of the furnace. It should be understood that the detection of such inner surface anomalies is indicative of problem areas within the furnace.

The inspection data collected by the ultrasonic transducers may also be used to identify the locations of the bends of the furnace and, thus, assist in correlating the inspection data to the physical geometry of the furnace. For example, a decrease in the number of inside radius readings and/or wall thickness readings within a particular time interval may provide a "data clue" as to the location of a bend. Missing data is more likely in a bend due to the fact that one or more of the transducers may not receive sufficient energy when the angle between the transducer and the inner wall of the furnace changes by more than a few degrees. Also, an increase in the variation of the inside radius readings and/or wall thickness readings within a particular time interval may provide another "data clue" as to the location of a bend. This is due to the fact that the readings from a particular transducer are more likely to vary from the readings of the other transducers as the inspection tool traverses a bend. In addition, the readings may be used to detect a change in the centering of the inspection tool to provide yet another "data clue" as to the location of a bend.

Another type of device that may be used to collect inspection data from the furnace is a laser profilometer. A laser profilometer is operable to map the inner wall of the furnace by projecting a focused beam of light onto the surface and imaging its movement onto a position sensitive photosensor. The laser profilometer rotates as the inspection tool progresses though the furnace, thus creating a helical scan of the inner wall of the furnace. The result is a digital, high resolution image of the inner wall of the furnace that provides more accurate inside radius readings (as well as a larger number of inside radius readings for a given surface area) as compared to the ultrasonic transducers described above. These readings may also be used to detect a change in the centering of the inspection tool and, thus, provide "data clues" as to the locations of the bends.

One or more auxiliary sensors may also be incorporated into the inspection tool for the purpose of collecting sensor data from the furnace. The sensor data may also provide "data clues" as to the locations of the bends and, thus, assist in correlating the inspection data to the physical geometry of the furnace. The sensor data is preferably collected simultaneously with the inspection data to assure that all of the data can be correlated in time.

One type of auxiliary sensor that may be used to collect sensor data from the furnace is an axial encoder. An axial encoder has roller wheels that contact the inner wall of the furnace and rotate as the inspection tool progresses through the furnace. Each output pulse from the axial encoder indicates that the inspection tool has moved a predetermined distance through the furnace (such as ¼ inch or ½ inch). In a time-based collection system, these output pulses are used to increment a counter that is read at each of the predetermined time intervals, whereby the counter readings are stored in the memory of the inspection tool. It should be understood that these counter readings may be converted to distance readings and then used in combination with the known geometry of the furnace to identify the locations of the bends. Preferably, two axial encoders are employed to provide redundancy in the event that one becomes stuck as the inspection tool progresses through the furnace.

One skilled in the art will understand that an axial encoder may not provide an accurate measurement of the location of the inspection tool within the furnace. Typically, an axial encoder has a position error that is 2% to 4% the length of the furnace. For example, a 10,000 foot long furnace will typically result in a position error of 200 feet to 400 feet. This position error will not be consistent, but will vary based on the frictional characteristics of different sections of the furnace. Because an axial encoder may not provide accurate "data clues" as to the locations of the bends, other types of auxiliary sensors should preferably be used in conjunction with the axial encoder to assist in identifying the locations of the bends.

Another type of auxiliary sensor that may be used to collect sensor data from the furnace is an accelerometer. An accelerometer is operable to detect an acceleration (i.e., change in speed) of the inspection tool, which is more likely to occur in the bends. In a time-based collection system, the voltage of the accelerometer is read at each of the predetermined time intervals, whereby the voltage readings are stored in the memory of the inspection tool. It should be understood that these voltage readings may be converted to acceleration readings to thereby identify the locations of the bends. Of course, if the inspection tool is designed to flow reliably through the furnace, the acceleration in the bends may not be significantly different from other accelerations that the inspection tool might encounter. In these instances, the accelerometer may not provide accurate "data clues" as to the locations of the bends and, as such, other types of auxiliary sensors should preferably be used.

It should be understood that the devices described above (namely, one or more ultrasonic transducers, a laser profilometer, an axial encoder, and an accelerometer) are merely examples of the types of devices that may be incorporated into the inspection tool. One skilled in the art will appreciate that many other types of devices could also be used, such as a roll encoder, a gyroscope or an inertial navigation system. In addition, the number of devices incorporated into the inspection tool may vary from a single device (e.g., a laser profilometer) to several devices (e.g., an array of ultrasonic transducers and several auxiliary sensors). Thus, any type and number of devices may be used to collect inspection data and/or sensor data from the furnace in accordance with the present invention.

Figure 2:
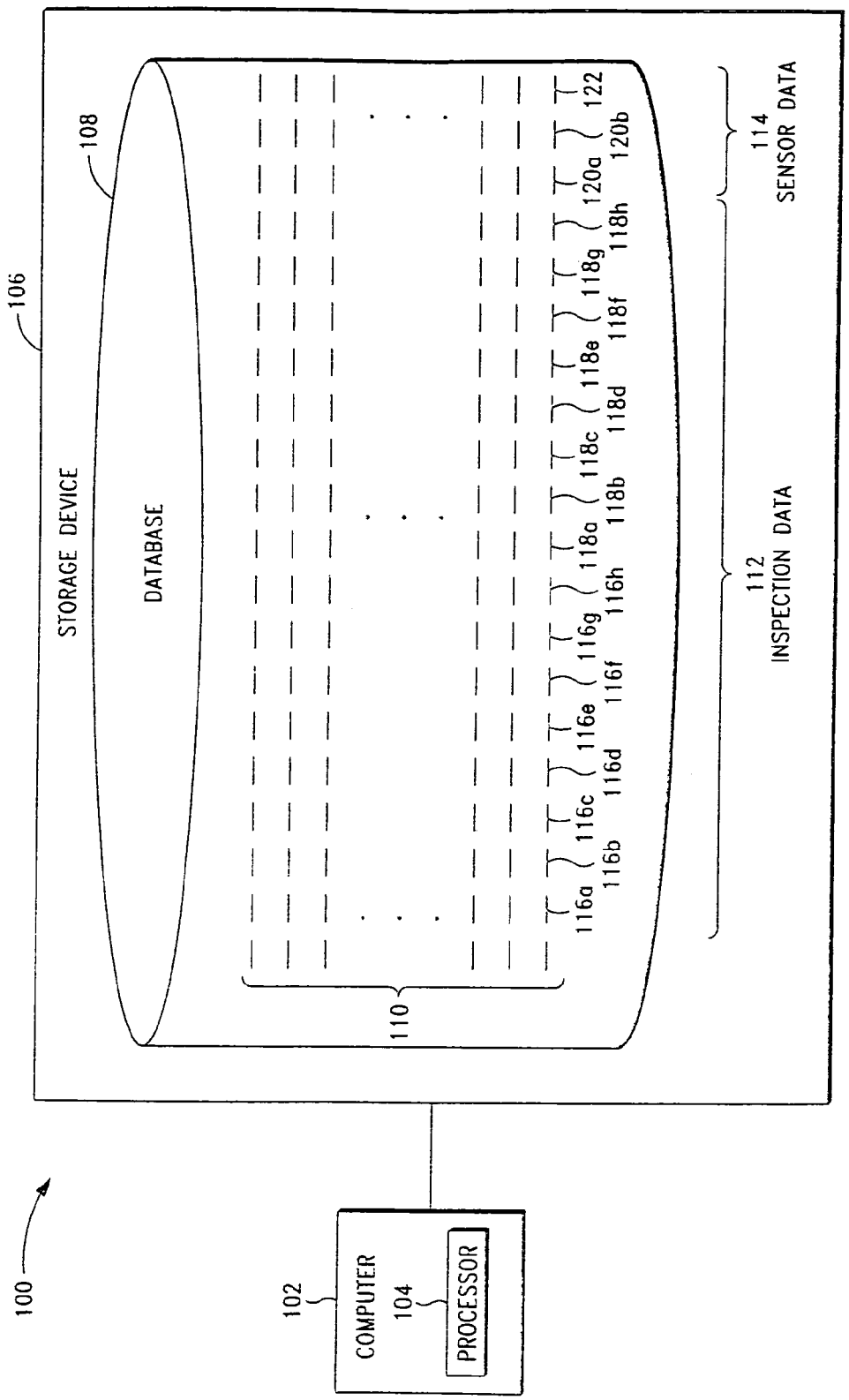
FIG. 2 is a block diagram of a computer system for displaying inspection data in accordance with the present invention.

Referring now to FIG. 2, an exemplary embodiment of a system that may be used in accordance with the present invention is designated generally as reference numeral 100. System 100 comprises a computer 102 that is programmed to perform various processes (each of which will be described in detail hereinbelow). To perform these processes, computer 102 includes a processor 104 that is operable to execute computer-readable instructions stored on a computer-readable medium. The computer-readable instructions are preferably coded using the MatLab programming language, although other programming languages could also be used, such as C, C++, C # and Java. The computer-readable medium may comprise any type of computer memory, such as floppy disks, conventional hard disks, CD-ROMS, flash ROMS, nonvolatile ROM and. RAM. Examples of computers that are suitable for use with the present invention include personal computers, server computers and multiprocessor computers, although other types of computers could also be used.

Referring still to FIG. 2, system 100 also comprises a storage device 106, wherein computer 102 is programmed to maintain in storage device 106 a database 108 that identifies various types of relational data. In this embodiment, the relational data comprises a plurality of time intervals 110 and corresponding inspection data 112 and sensor data 114 that have been downloaded from the memory of the inspection tool during each of the time intervals (as described above). The relational data is preferably maintained in a single table within database 108, although other database configurations could also be used. It should be understood that computer 102 may include any relational database software that is suitable for maintaining database 108 in storage device 106.

In the exemplary embodiment of FIG. 2, inspection data 112 comprises a plurality of inspection readings collected from the furnace by an array of eight (8) ultrasonic transducers, namely, eight (8) wall thickness readings 116a-116h and eight (8) inside radius readings 118a-118h for each of time intervals 110. Sensor data 114 comprises a plurality of sensor readings collected from the furnace by a pair of axial encoders and an accelerometer, namely, two (2) position readings 120a and 120b and one (1) acceleration reading 122 for each of time intervals 110. Thus, it can be seen that each of time intervals 110 contains a total of nineteen (19) different readings collected from the furnace during that particular time interval. Of course, it should be understood that many different types of devices could be incorporated into the inspection tool such that the width of the data set will vary between different applications.

In accordance with one approach to implementing the present invention, computer 102 is programmed to generate a display of all of inspection data 112 collected from the furnace. A data analyst may then analyze the display of inspection data 112 (preferably in conjunction with sensor data 114) in order to identify the locations of the furnace bends. Then, based upon input from the data analyst, computer 102 is preferably programmed to generate a plurality of data markers that identify the locations of the furnace bends. Preferably, visual indicators of such data markers are shown on the display in relation to inspection data 112. Computer 102 may also be programmed to partition inspection data 112 at the data markers so as to correlate inspection data 112 to the appropriate tube segments of the furnace. Finally, a data analyst may view the display of inspection data 112 to visually detect problem areas within the furnace so that the appropriate tube segments may be repaired or replaced by the plant maintenance personnel. Examples of this approach will be described with reference to "Example 1," "Example 2," and "Example 3" below.

In accordance with another approach to implementing the present invention, computer 102 is programmed to analyze inspection data 112 and/or sensor data 114 and then, based upon this analysis, automatically generate a plurality of data markers that identify the locations of the furnace bends. Computer 102 is also programmed to partition inspection data 112 at the data markers so as to correlate inspection data 112 to the appropriate tube segments of the furnace. Computer 102 is further programmed to generate a display of the partitioned inspection data 112, wherein the display is a two-dimensional or three-dimensional representation of one or more of the tube segments of the furnace. Finally, a data analyst may view this display to visually detect problem areas within the furnace so that the appropriate tube segments may be repaired or replaced by the plant maintenance personnel. An example of this approach will be described with reference to "Example 4" below.

With both approaches, the locations of the furnace bends may be identified by detecting one or more "data clues" in inspection data 112 and/or sensor data 114 collected from the furnace. Examples of these "data clues" include an increase in the variation of wall thickness readings 116a-116h and/or inside radius readings 118a-118h within a particular time interval 110, a decrease in the number of wall thickness readings 116a-116h and/or inside radius readings 118a-118h within a particular time interval 110, and/or a change in the centering of the inspection tool. All of these conditions are more likely to occur in the furnace bends.

Also, position readings 120a and 120b may be used to determine the distance traveled by the inspection tool during each of time intervals 110, which may be compared with the known geometry of the furnace to assist in identifying the locations the furnace bends. In addition, acceleration readings 122 may be used to determine the acceleration of the inspection tool during each of time intervals 110 to thereby assist in identifying the locations of the furnace bends. Of course, it should be understood that other types of "data clues" may also be used to identify the locations of the furnace bends in accordance with the present invention.

In accordance with yet another approach to implementing the present invention, the data markers are included within the data set downloaded from the inspection tool. For example, one or more of the sensors may be sufficiently reliable so as to detect the location of each physical feature, whereby a "1" in the data set indicates the detection of a physical feature and a "0" in the data set indicates no detection of a physical feature. Computer 102 is then programmed to partition inspection data 112 at the data markers so as to correlate inspection data 112 to the physical geometry of the furnace. Computer 102 is also programmed to generate a display of the partitioned inspection data 112, wherein the display is a two-dimensional or three-dimensional representation of one or more of the tube segments of the furnace. Finally, a data analyst may view this display to visually detect problem areas within the furnace so that the appropriate tube segments may be repaired or replaced by the plant maintenance personnel.

To enhance the ability of a data analyst to visually detect problem areas within the furnace, it is preferable to remove the effects of tool de-centering from the display of the inspection data. Although the tool geometry keeps the inspection tool approximately centered in the pipe as the tool traverses the furnace, gravity often causes the inspection tool to ride below the centerline in horizontal pipes. In addition, when traversing a bend, the inspection tool has a tendency to push to one side as it enters the bend. If the inspection tool is perfectly centered in a round pipe, each ultrasonic transducer will measure the same distance to the inner wall of the pipe (assuming there is no pitting or corrosion). However, if the inspection tool is de-centered, there will be a near-sinusoidal variation in the distance readings collected by each of the ultrasonic transducers around the circumference of the inspection tool. If the de-centering is a significant percentage of the pitting or corrosion to be measured, it is very difficult to accurately determine the pit depth or corrosion by simply looking at the displayed inspection data.

For this reason, the data set is preferably translated so that the data is displayed as if it had been collected from the centerline of the pipe. This centering process may use either the outside surface of the pipe or the inside surface of the pipe as the centering reference. If a data analyst is expecting corrosion on the inner wall of the pipe, the outside surface of the pipe is the preferred centering reference. However, if corrosion is expected on the outer wall of the pipe, the inside surface of the pipe is the preferred centering reference. In either case, the centering process is performed in order to reference the radius data (either inside radius data, or, outside radius data (i.e., inside radius plus wall thickness)) from the center of an undamaged pipe so as to visually emphasize problem areas in the furnace.

For round pipes, the centering process uses the radius data to compute a least squares fit to a circle. The radius reading that is furthest from the best fit circle is eliminated. The fitting process may then be repeated, whereby the next radius reading that is furthest from the best fit circle is eliminated. This fitting process may be further repeated until the remaining radius readings are within a preset threshold from the best fit circle. The fitting process generates the x,y location of the center of the pipe relative to the data set and a mean radius for the pipe. The original radius values are then translated to the pipe center by a vector addition of the computed x,y location of the center of the pipe with the radius readings. It should be understood that this fitting process can be performed using the inside radius data or the outside radius data.

In addition, for oval pipes or where the plant would like to compute the ovality of the pipe, the fitting process can be performed with an ellipse instead of a circle. This fitting process generates a major diameter, a minor diameter, an x,y location of the center of the pipe, and orientation. In addition, the fitting process can be extended to a cylinder where more than one slice of data is used in the fitting process.

Various examples will now be provided to further describe the furnace tube inspection system of the present invention. These examples are provided merely to illustrate different approaches that may be used to correlate the inspection data to the physical geometry of the furnace and display the inspection data in a manner that enables the visual detection of problem areas within the furnace. Of course, it should be understood that other approaches may also be used and these examples do not in any way limit the scope of the present invention.

EXAMPLE 1

In this example, computer 102 is programmed to generate a two-dimensional display of the wall thickness readings and/or inside radius readings collected from a furnace, which may be viewed by a data analyst in order to identify the locations of the furnace bends. Then, based upon input from the data analyst, computer 102 is programmed to generate a plurality of data markers on the display to thereby correlate the various readings to the appropriate tube segments of the furnace. After generation of the data markers, the data analyst may view the display in order to visually detect problems areas within the furnace. This example will now be described in greater detail with reference to FIGS. 3 and 4.

Figure 3:
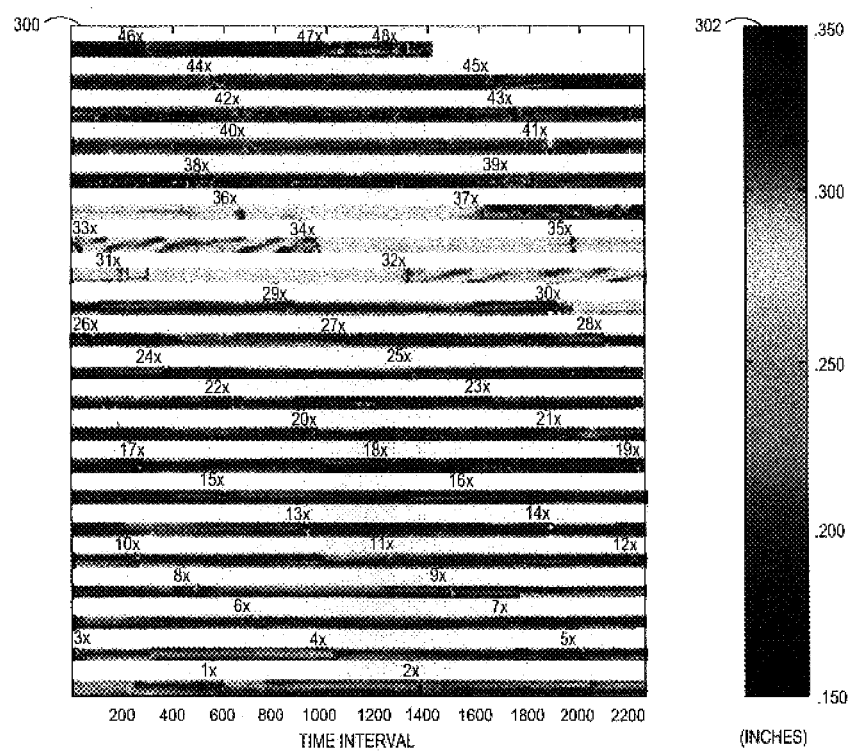
FIG. 3 is a two-dimensional color-coded strip chart generated by the computer system of FIG. 2, which shows all of the wall thickness readings collected from a furnace in accordance with a first example of the present invention.

Referring to FIG. 3, computer 102 is programmed to generate a strip chart 300 in which all of the wall thickness readings for a plurality of time intervals are plotted across a plurality of horizontal strips. The wall thickness readings are plotted successively in time from left-to-right and bottom-to-top. As such, the lower left-hand corner of the chart corresponds to the time when the inspection tool leaves the launcher (see FIG. 1A) and the upper right-hand corner of the chart corresponds to the time when the inspection tool reaches the receiver (see FIG. 1C). The wall thickness readings for each of the time intervals are plotted vertically across the height of the horizontal strips. It can be seen that the various wall thickness readings displayed on strip chart 300 are color-coded in accordance with a color legend 302. In this example, the wall thickness readings range from 0.15 inches (shown in dark blue) to 0.35 inches (shown in dark red).

Figure 4:
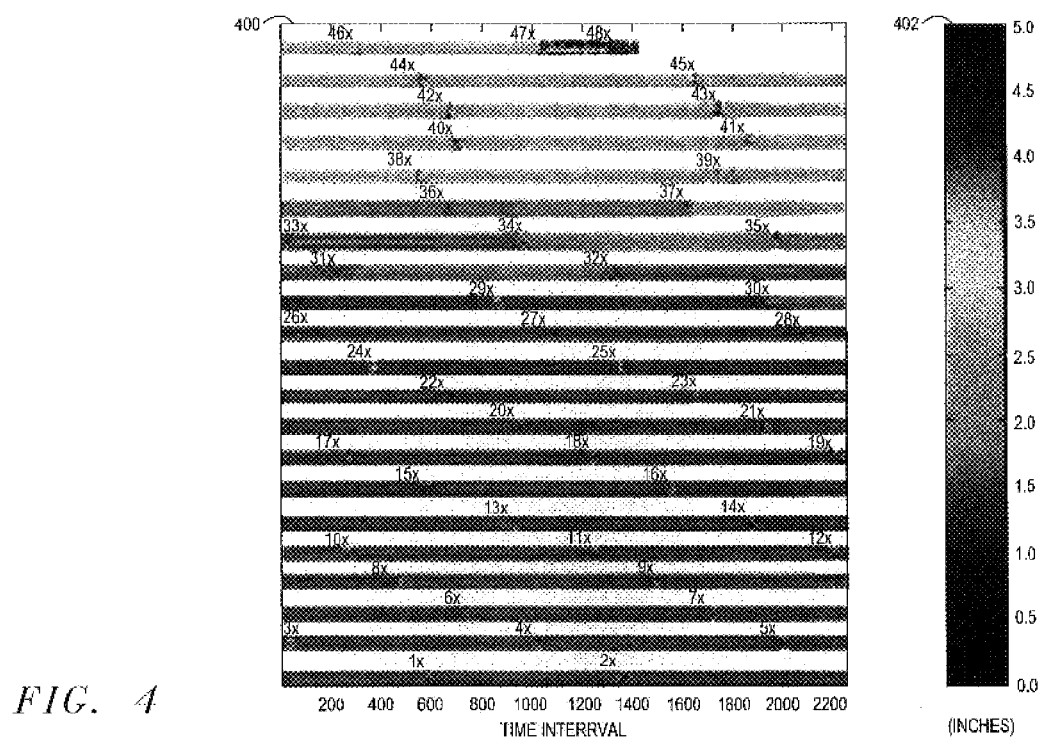
FIG. 4 is a two-dimensional color-coded strip chart generated by the computer system of FIG. 2, which shows all of the inside radius readings collected from a furnace in accordance with the first example of the present invention.

Referring to FIG. 4, computer 102 is also programmed to generate a strip chart 400 in which all of the inside radius readings for a plurality of time intervals are plotted across a plurality of horizontal strips. Again, the inside radius readings are plotted successively in time from left-to-right and bottom-to-top, and the inside radius readings for each of the time intervals are plotted vertically across the height of the horizontal strips. It can be seen that the various inside radius readings displayed on strip chart 400 are color-coded in accordance with a color legend 402. In this example, the inside radius readings range from 0.00 inches (shown in dark blue) to 5.00 inches (shown in dark red).

It should be understood that color legends 302 and 402 may be customized as desired for different applications. Furthermore, as an alternative to the use of color legends 302 and 402, the wall thickness readings and/or inside radius readings may be represented in gray scale (as opposed to color) on the strip charts. However, it can be appreciated that the use of color legends 302 and 402 is preferable to gray scale in order to readily "announce" differences between the various readings shown on the strip charts.

On strip charts 300 and 400, each horizontal strip represents a 60 second period of time. Assuming that the speed of the inspection tool is 2 ft/sec and the data collection rate is 38 Hz per transducer, it can be calculated that each horizontal strip displays the readings collected from 120 feet of furnace (i.e., 2 ft/sec×60 seconds) over 2,280 different time intervals (i.e., 38 Hz×60 seconds). Because of the large number of readings displayed on strip charts 300 and 400, a zoom function is provided that allows a data analyst to examine desired sections of the horizontal strips in greater detail.

In this example, a data analyst analyzes strip chart 300 and/or strip chart 400 in order to identify the locations of the furnace bends. As discussed above, the locations of the furnace bends may be identified by visually detecting one or more "data clues" on the strip charts. These "data clues" may comprise an increase in the variation of the wall thickness readings and/or inside radius readings within a particular time interval (which will be depicted as different colors across the height of a horizontal strip) and/or a decrease in the number of wall thickness readings and/or inside radius readings within a particular time interval (which will be depicted as white spaces or gaps across the height of a horizontal strip).

While analyzing strip chart 300 and/or strip chart 400, the data analyst moves a mouse across the horizontal strips and marks the locations of the furnace bends by clicking on the appropriate positions on the strip charts. Based upon this input from the data analyst, computer 102 is programmed to generate the data markers and place a roman numeral (signifying the tube segment number) followed by an "x" above the positions marked by the data analyst. The various readings are thus partitioned at the data markers to thereby correlate the readings to the appropriate tube segments of the furnace.

Preferably, the data analyst will analyze strip chart 300 and/or strip chart 400 in conjunction with a mechanical drawing of the physical layout of the furnace to provide hints as to where the bends or ends of the tube segments should be located. As noted above, the physical geometry of a furnace is not always consistent such that either the wall thickness or the inside radius of the furnace may change from one tube segment to another. For example, it is apparent from strip chart 300 that tube segments 1 through 30 have generally one wall thickness, tube segments 31 through 37 have generally another wall thickness, and tube segments 38 through 47 have generally another wall thickness. Similarly, it is apparent from strip chart 400 that tube segments 1 through 37 have generally one inside radius, while tube segments 38 through 47 have generally another inside radius. It should be understood that the known lengths of the various tube segments may be superimposed upon strip charts 300 and 400 to provide additional guidance in identifying the locations of the bends or ends of the tube segments.

It can be seen that strip charts 300 and 400 readily "announce" problems areas within the furnace. For example, it is apparent from strip chart 300 that the wall thickness readings vary in tube segments 33 and 34 and to a lesser extent in tube segments 31, 36 and 37 (as shown by the yellow and red variations in color along the length of these tube segments). In addition, the green-colored areas in tube segments 32 and 35 may indicate problem areas within these tube segments. These variations were immediately apparent with no more than a glance at strip chart 300. Potential problem areas can also be seen from strip chart 400. For example, the yellow areas along the top of tube segments 38 through 47 may be indicative of corrosion within these tube segments. Using strip charts 300 and 400, the data analyst can determine that one or more of the tube segments are flawed and should be repaired or replaced by the plant maintenance personnel.

It should be understood that strip charts 300 and 400 are merely examples of the types of displays that may be used to visually detect problem areas within the furnace. For example, after generation of the data markers, the wall thickness readings and/or inside radius readings could be displayed as a stacked set of bars wherein each bar represents one tube segment of the furnace. Also, the wall thickness readings and/or inside radius readings could be displayed in a three-dimensional format in which the structure of the tube segments matches the actual physical geometry of the furnace. One skilled in the art will understand that other types of displays may also be used in accordance with the present invention.

EXAMPLE 2

Figure 5:
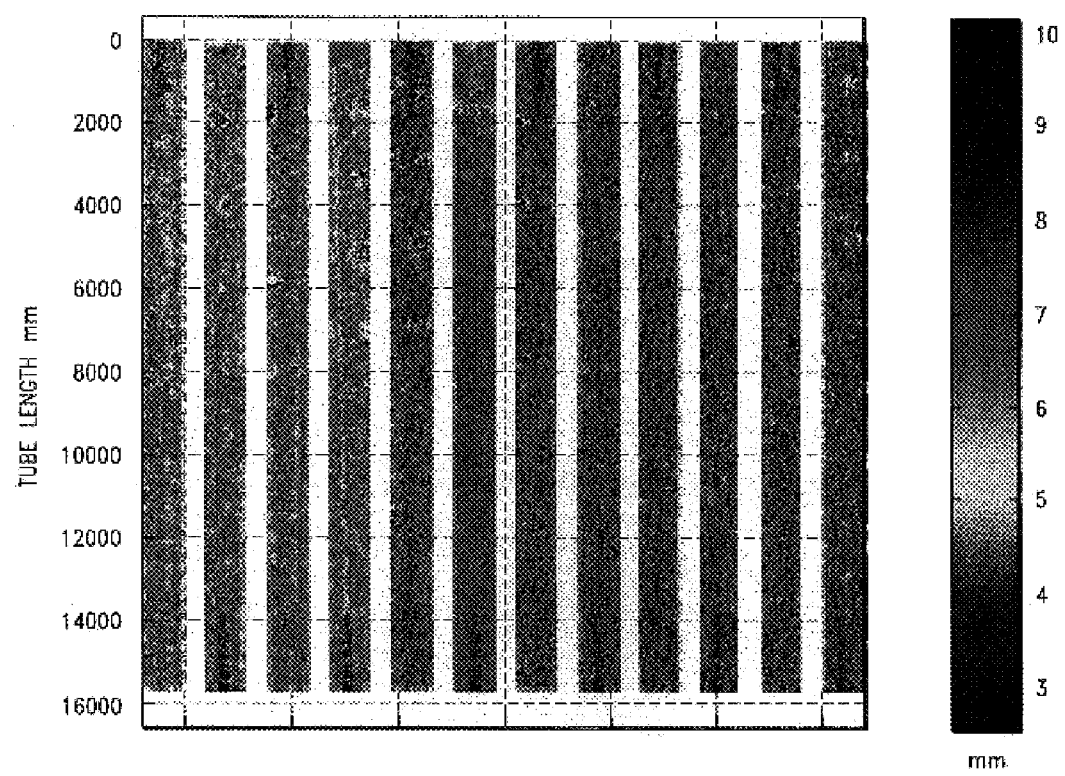
FIG. 5 is a two-dimensional color-coded chart generated by the computer system of FIG. 2, which shows all of the wall thickness readings collected from a convection section of a furnace in accordance with a second example of the present invention.

In this example, computer 102 is programmed to generate a two-dimensional display of the wall thickness readings collected from the convection section of a furnace, whereby the display may be viewed by a data analyst in order to visually detect problems areas within the furnace. Specifically, computer 102 is programmed to generate the chart shown in FIG. 5, in which all of the wall thickness readings for a plurality of time intervals are plotted across a plurality of vertical bars. Each vertical bar displays the wall thickness readings from a single tube segment. The tube segments are positioned in their proper orientation (but with the connecting bends removed).

In this example, the wall thickness readings displayed on the chart are color-coded in accordance with a color legend, wherein the readings range from 3 mm (shown in dark red) to 10 mm (shown in dark blue). It should be understood that the wall thickness readings may alternatively be represented in gray scale (as opposed to color) on the chart. However, it can be appreciated that the use of a color legend is preferable to gray scale in order to readily "announce" differences between the various readings shown on the chart.

When viewing all of the tube segments in their proper orientation, a data analyst can determine that the blue speckles on the chart are caused by the pins welded on the outside of the tube segments (which are used to increase the heat transfer area). The data analyst can also determine that the red blotches on the chart indicate areas of external corrosion on the tube segments. In this example, the spacing between the red blotches indicates that the source of the problem is a slow leaking fixture located above the tube segments that is dripping fluid onto the furnace. Thus, both the problem areas of the furnace and their source can be readily determined from the chart of FIG. 5.

EXAMPLE 3

Figure 6:
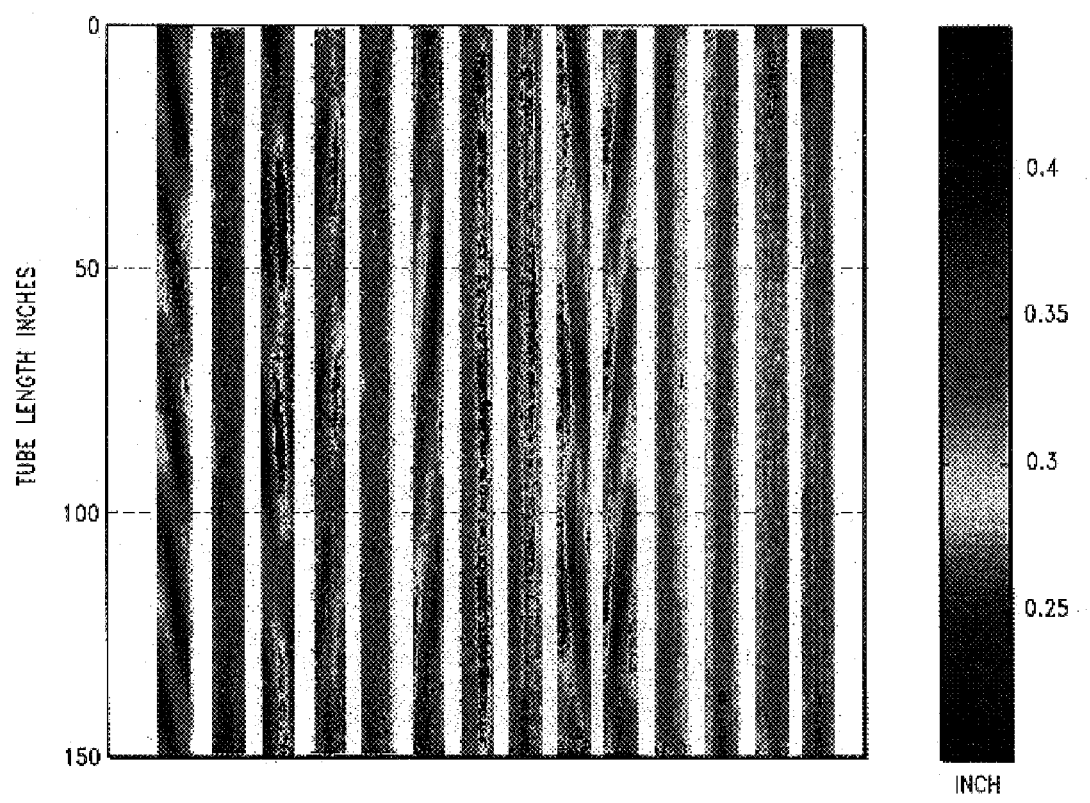
FIG. 6 is a two-dimensional color-coded chart generated by the computer system of FIG. 2, which shows all of the wall thickness readings collected from a convection section of a furnace in accordance with a third example of the present invention.

In this example, computer 102 is programmed to generate a two-dimensional display of the wall thickness readings collected from the convection section of another furnace, whereby the display may be viewed by a data analyst in order to visually detect problems areas within the furnace. Specifically, computer 102 is programmed to generate the chart shown in FIG. 6, in which all of the wall thickness readings for a plurality of time intervals are plotted across a plurality of vertical bars. Similar to the chart of FIG. 5, each vertical bar displays the wall thickness readings from a single tube segment, wherein the tube segments are positioned in their proper orientation (but with the connecting bends removed).

In this example, the wall thickness readings displayed on the chart are color-coded in accordance with a color legend, wherein the readings range from 0.20 inches (shown in dark red) to 0.45 inches (shown in dark blue). Again, while the wall thickness readings may alternatively be represented in gray scale (as opposed to color) on the chart, the use of a color legend is preferable to gray scale in order to readily "announce" differences between the various readings shown on the chart.

When viewing all of the tube segments in their proper orientation, a data analyst can determine that the swirling patterns on the chart are indicative of general wall thinning caused by flow patterns within the furnace. It should be noted that the swirling patterns are not caused by the rotation of the inspection tool within the furnace because the inside radius readings (not shown) do not indicate such rotation. Also, the inspection tool is typically de-centered in the furnace due to gravity. Thus, if the inspection tool is rotating, the readings of the ultrasonic transducer located closest to the inner wall of the furnace would change (which is not the case here). Thus, in this example, the problem areas caused by the flow patterns within the furnace readily announce themselves on the chart of FIG. 6.

EXAMPLE 4

In this example, computer 102 is programmed to analyze inspection data and sensor data collected from a furnace in order to automatically generate a plurality of composite data markers (which are derived from a plurality of individual data markers) that identify the locations of the furnace bends. Computer 102 is also programmed to partition the inspection data at the composite data markers to thereby correlate the inspection data to the appropriate tube segments of the furnace. Computer 102 is further programmed to generate a display of the partitioned inspection data that may be viewed by a data analyst in order to visually detect problem areas within the furnace. This example will now be described in greater detail with reference to FIGS. 7, 8 and 9.

Figure 7:
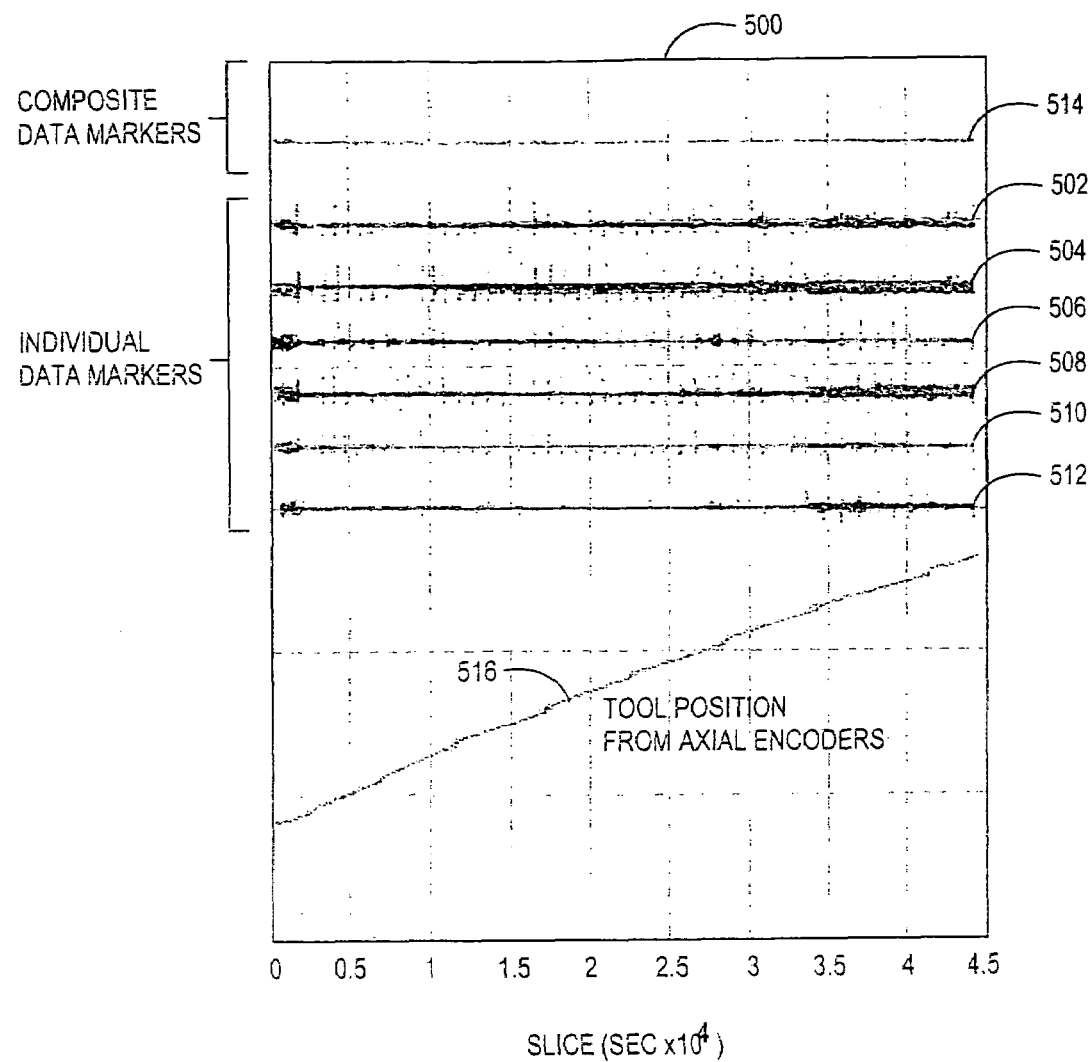
FIG. 7 is a colorized chart generated by the computer system of FIG. 2, which shows the individual data markers and composite data markers that may be used to identify the locations of the furnace bends in accordance with a fourth example of the present invention.

Referring to FIG. 7, computer 102 is programmed to generate a chart 500 in which a plurality of individual data markers are plotted on lines 502, 504, 506, 508, 510 and 512 and a plurality of composite data markers are plotted on line 514. Computer 102 is programmed to automatically generate the individual data markers on lines 502, 504, 506, 508, 510 and 512 based upon the detection of various "data clues" in the inspection data and sensor data. Each of these lines are described below:

Line 502 represents the individual data markers generated by detecting a decrease in the number of wall thickness readings within a particular time interval.

Line 504 represents the individual data markers generated by detecting a decrease in the number of inside radius readings within a particular time interval.

Line 506 represents the individual data markers generated by detecting an increase in the variation of wall thickness readings within a particular time interval.

Line 508 represents the individual data markers generated by detecting an increase in the variation of inside radius readings within a particular time interval.

Line 510 represents the individual data markers generated by detecting the de-centering of the inspection tool within a particular time interval.

Line 512 represents the individual data markers generated by detecting an acceleration of the inspection tool within a particular time interval.

It can be seen that the location of each of the individual data markers is shown by a spike on lines 502, 504, 506, 508, 510 and 512, wherein the length of the spike above the line (i.e., on the positive side of the line) is an indicator of the degree of reliability for that individual data marker. In other words, higher spikes have a higher degree of reliability than lower spikes.

Computer 102 is also programmed to automatically generate the composite data markers on line 514 by combining the individual data markers shown on lines 502, 504, 506, 508, 510 and 512. In this example, the individual data markers are normalized so that one data marker does not dominate the other data markers within a particular time interval. As an example, for an N×M array of either wall thickness readings or inside radius readings (where N=the number of slices taken at a rate of 38 Hz and M=the number of ultrasonic transducers), each of the individual data markers may be normalized by dividing the array element by the maximum value found in the array. Then, the normalized individual data markers are combined using a root mean square calculation to generate the composite data markers (although other types of calculations or algorithms could also be used). Again, it can be seen that the location of each of the composite data markers is shown by a spike on line 514, wherein the length of the spike above the line (i.e., on the positive side of the line) is an indicator of the degree of reliability for that composite data marker. Of course, it should be understood that the composite data markers provide a higher degree of reliability than any of the individual data markers alone.

It should be noted that chart 500 also includes line 516, which is a plot of the position of the inspection tool as derived from the integral count from the axial encoders. Line 516 may be used to verify that the inspection tool did not become stuck at any point within the furnace. In this example, there are no flat sections along line 516 as would occur if the inspection tool had become stuck. If one or more flat sections were present, a data analyst could manually remove the redundant data collected during that particular time interval.

Figure 8:
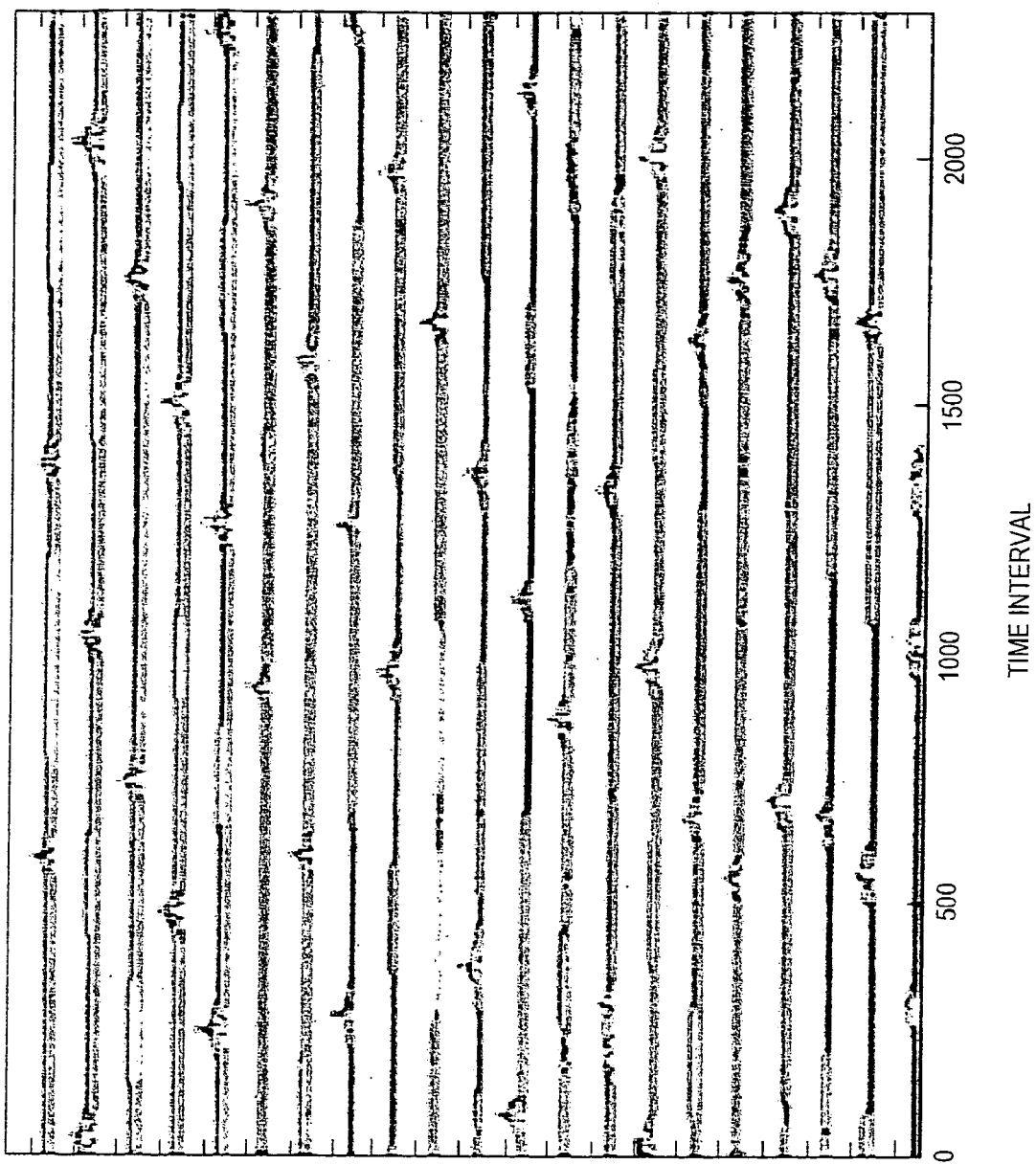
FIG. 8 is a colorized chart generated by the computer system of FIG. 2, which shows the composite data markers in relation to an adaptive threshold that may be used to identify the locations of the furnace bends in accordance with the fourth example of the present invention.

Referring to FIG. 8, computer 102 is also programmed to generate a chart that depicts all of the composite data markers in relation to a predetermined threshold. Specifically, all of the composite data markers shown on line 514 of chart 500 are plotted successively in time from left-to-right and top-to-bottom to form the green line shown on the chart of FIG. 8. By contrast, the blue line shown on this chart represents a predetermined threshold that may be used to determine if the composite data markers are "valid" indicators of the locations of the furnace bends. In other words, a composite data marker is "valid" when the peak is located above the predetermined threshold and "invalid" when the peak is located below the predetermined threshold.

As an example, the predetermined threshold may be generated by: (1) applying a 50 point running average filter in both directions through the composite data markers (C_Data$_N$) to generate a base signal (Base$_N$), wherein running the filter in both directions removes the time delay; (2) computing a running standard deviation of the composite data markers (C_Data$_N$) with a block size of 1000 to create a standard deviation array (STDArray$_N$); and (3) computing a threshold array (Thresh$_N$) by adding the base signal (Base$_N$) to 2.5 times the standard deviation array (STDArray$_N$) (i.e., Thresh$_N$=Base$_N$+2.5*STDArray$_N$). One skilled in the art will appreciate that a data analyst may analyze the chart of FIG. 8 in order to modify or "tweak" the algorithm used to generate the predetermined threshold.

In this example, the composite data markers shown in FIGS. 7 and 8 comprise pointers operable to "point to" the positions in the database that correspond to the locations of the furnace bends. Alternatively, the composite data markers may be directly embedded within the database, or, may comprise file names for the various inspection data. Furthermore, a data analyst may simply use the composite data markers as a guide to partition the inspection data (described below). Of course, other types of composite data markers may also be used to correlate the inspection data to the physical geometry of the furnace in accordance with the present invention.

After generation of the composite data markers, computer 102 is programmed to partition the inspection data at the composite data markers so as to correlate the inspection data to the appropriate tube segments of the furnace. Computer 102 is also programmed to generate a display of the partitioned inspection data that may be viewed by a data analyst in order to visually detect problem areas within the furnace. This display may comprise a two-dimensional or three-dimensional representation of one or more of the tube segments of the furnace, which may be customized in accordance with customer requirements. For example, one customer may require a display that shows the wall thickness at five equally spaced positions along the length of a specific tube segment, while another customer may require a display that shows the minimum wall thickness for each tube segment of the furnace. Of course, this information may also be provided to the customer in the form of a written report that accompanies the display.

Figure 9:
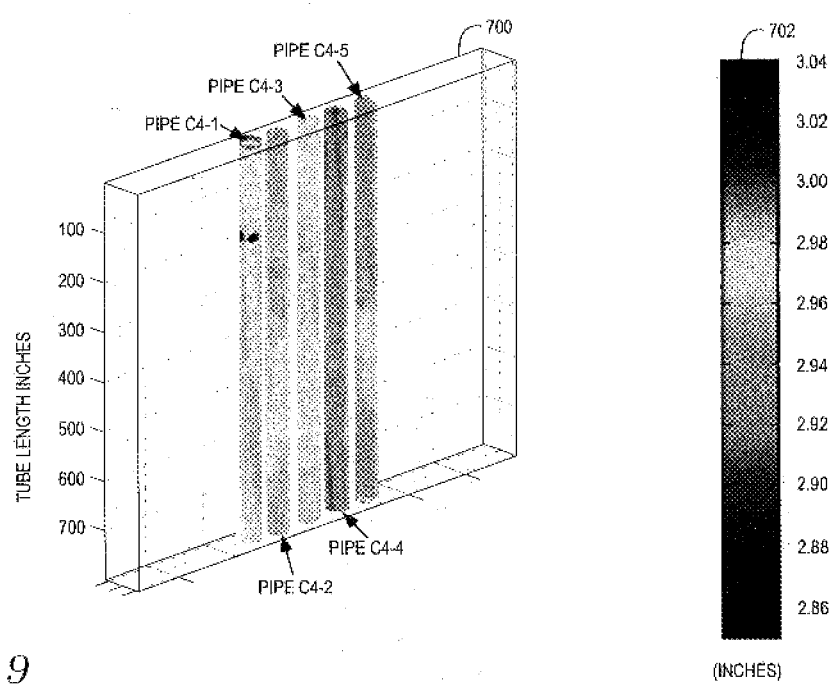
FIG. 9 is a three-dimensional color-coded chart generated by the computer system of FIG. 2, which shows various tube segments of a furnace with the connecting bends removed in accordance with the fourth example of the present invention.

An example of a display that may be customized in accordance with particular customer requirements is shown in FIG. 9. This display comprises a three-dimensional color-coded chart 700 that depicts the inside radius readings for five different tube segments of interest (with the connecting bends removed). The tube segments are displayed in a manner that matches the actual physical geometry of the furnace, and are labeled in accordance with the customer designations for those tube segments (i.e., PIPE C4-1, PIPE C4-2, PIPE C4-3, PIPE C4-4 and PIPE C4-5). It can be seen that the various inside radius readings displayed on chart 700 are color-coded in accordance with a color legend 702. In this example, the inside radius readings range from 2.86 inches (shown in dark blue) to 3.04 inches (shown in dark red).

It can be seen that chart 700 readily "announces" problems areas within the five tube segments of interest. For example, it is apparent from chart 700 that that the inside radius readings vary in the tube segments labeled PIPE C4-1, PIPE C4-2, PIPE C4-3 and PIPE C4-5 (as shown by the yellow and blue variations in color within these tube segments). These variations were immediately apparent with no more than a glance at chart 700. Thus, using chart 700, a data analyst can determine that one or more of these tube segments are flawed and should be repaired or replaced by the plant maintenance personnel.

Figure 10A:
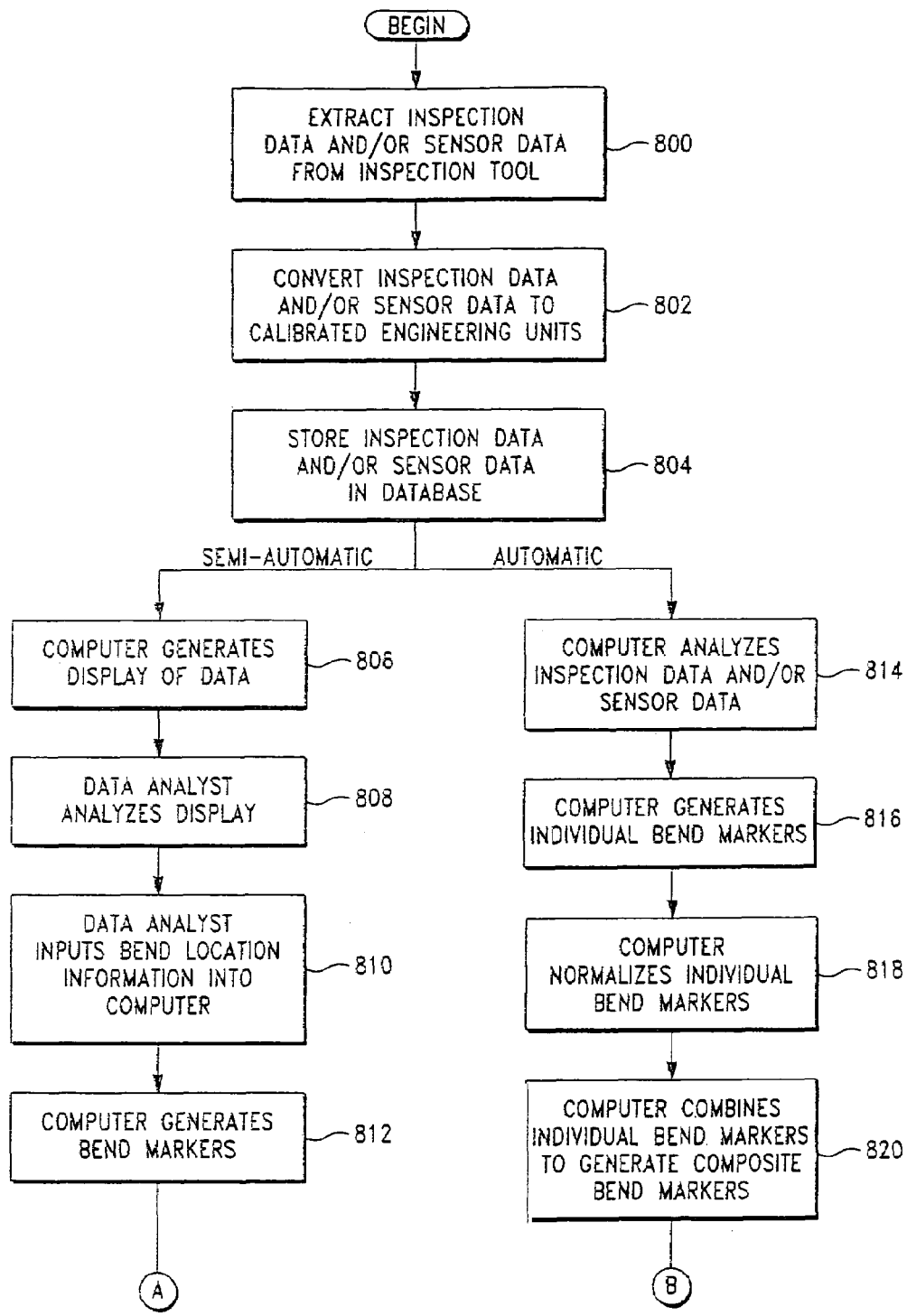
FIGS. 10A and 10B are flow charts of a method for displaying inspection data in accordance with the present invention.
Figure 10B:
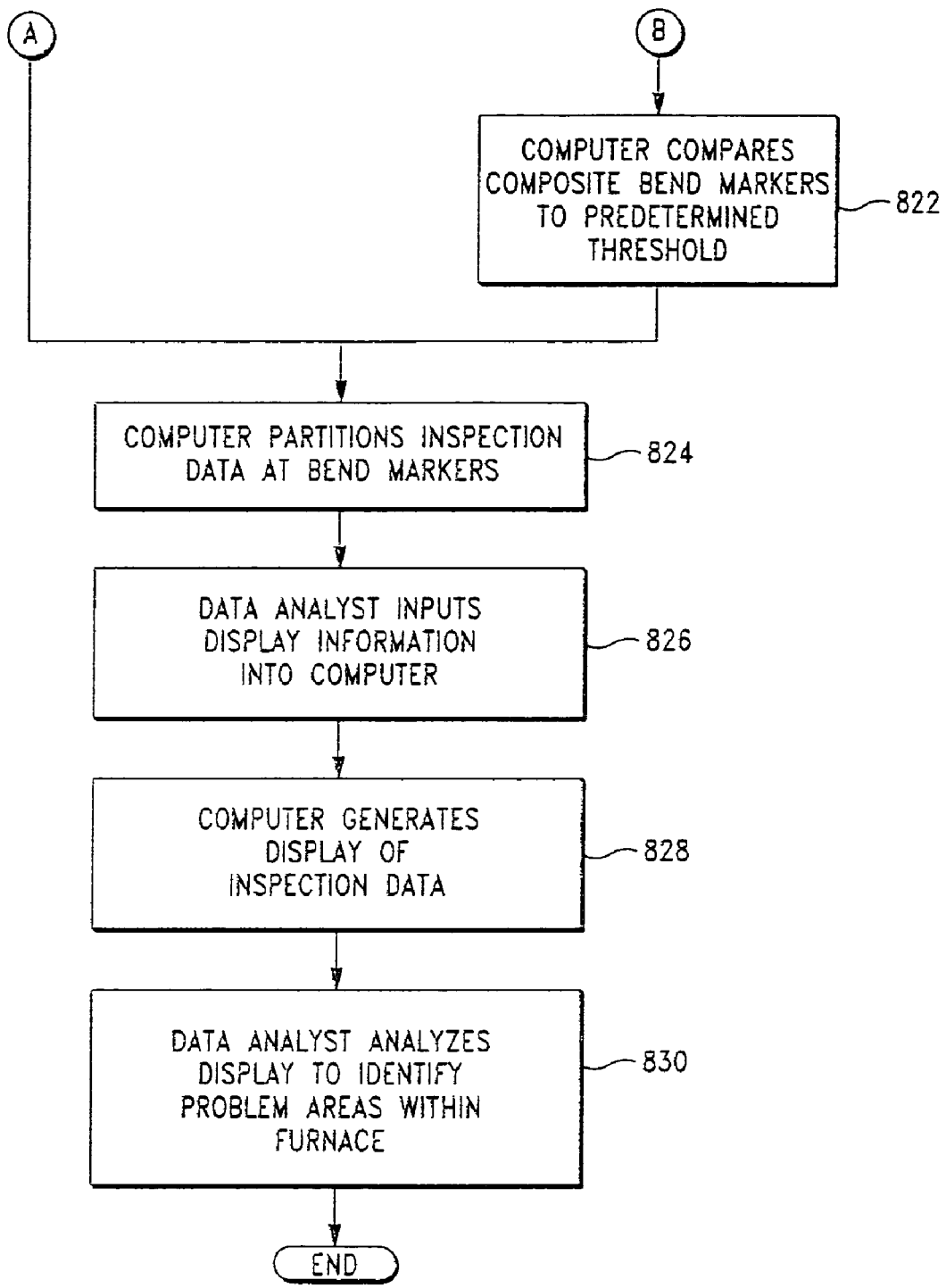

Referring to the flow charts of FIGS. 10A and 10B, an exemplary embodiment of the method of the present invention will now be described with reference to steps 800-830. First, in step 800, the inspection data and/or sensor data collected from the furnace is extracted from the inspection tool. Next, in step 802, the extracted inspection data and/or sensor data is converted to calibrated engineering units. For example, the readings collected by an ultrasonic transducer are converted from time to distance (e.g., inches), the readings collected by an axial encoder are converted from counter values to distance (e.g., inches), and the readings collected by an accelerometer are converted from voltage to acceleration (e.g., ft/sec$^2$). The conversions for other types of readings will be apparent to one skilled in the art. Then, in step 804, the converted inspection data and/or sensor data is stored in a database. Of course, it should be understood that steps 800-804 would not be necessary for the analysis of data sets that have been previously acquired and stored in a database.

Next, a plurality of data markers are generated that identify the locations of the furnace bends in relation to the inspection data stored in the database. The data markers may be generated either "semi-automatically" in steps 806 through 812 or "automatically" in steps 814 through 822.

Using the "semi-automatic" approach, in step 806, a computer is used to generate a two-dimensional or three-dimensional display that depicts some or all of the inspection data stored in the database (preferably on a single page). In step 808, a data analyst views and analyzes the display in order to visually detect "data clues" that assist in identifying the locations of the furnace bends. Then, in step 810, the data analyst inputs information into the computer that identifies the locations of the furnace bends. Finally, in step 812, the computer generates the data markers based upon the input from the data analyst.

Using the "automatic" approach, in step 814, a computer is used to analyze the inspection data and/or sensor data stored in the database in order to automatically generate a plurality of data markers. As shown in steps 816 through 820, this analysis may comprise generating a plurality of individual data markers based upon the detection of "data clues" in the inspection data and/or sensor data, normalizing the individual data markers, and then combining the individual data markers to generate a plurality of composite data markers. Then, in step 822, the computer may compare the composite data markers against a predetermined threshold to determine if the composite data markers are "valid" indicators of the locations of the furnace bends.

Once the data markers have been generated (either "semi-automatically" in steps 806 through 812 or "automatically" in steps 814 through 822), the inspection data is partitioned at the data markers so as to correlate the inspection data to the appropriate tube segments of the furnace in step 824. Then, in step 826, the data analyst inputs information relating to the display of the partitioned inspection data. This information may include customer requirements relating to the desired type of display (e.g., two-dimensional format or three-dimensional format) and the desired tube segments to be displayed (e.g., all of the tube segments or specific tube segments). In step 828, the computer generates the display in accordance with the customer requirements. Finally, in step 830, the data analyst views and analyzes the display in order to identify overall trends in the inspection data and/or to visually detect problem areas within the furnace.

While the present invention has been described and illustrated hereinabove with reference to exemplary embodiments, it should be understood that various modifications could be made to these embodiments without departing from the scope of the invention. Therefore, the invention is not to be limited to the exemplary embodiments described and illustrated hereinabove, except insofar as such limitations are included in the following claims.

What is claimed and desired to be secured by Letters Patent is as follows:

1. A system for displaying inspection data collected from a furnace with a specified physical geometry, wherein said furnace comprises a plurality of tube segments interconnected by a plurality of bends so as to allow stacking of at least a portion of said tube segments, said system comprising:
    a storage device for storing said inspection data; and
    a computer programmed to:
        partition said inspection data at a plurality of data markers each of which identifies a location of a physical feature of said furnace so as to correlate said inspection data to said physical geometry of said furnace;
        generate a display of at least a portion of said partitioned inspection data arranged to represent said physical geometry of a plurality of said tube segments and enable visual detection of a problem area comprising one or more of said tube segments; and
    wherein said inspection data is collected by one or more devices selected from the following group: an ultrasonic transducer, a laser profilometer, and combinations thereof.

2. The system of claim 1, wherein said display is comprised of a two-dimensional or three-dimensional representation of one or more of said tube segments of said furnace.

3. The system of claim 1, wherein said computer is further programmed to generate said data markers based upon input from a data analyst.

4. The system of claim 1, wherein said computer is further programmed to analyze said inspection data and generate said data markers based upon said analysis of said inspection data.

5. The system of claim 4, wherein said inspection data comprises a plurality of readings selected from the following group: wall thickness readings of said furnace, inside radius readings of said furnace, and combinations thereof.

6. The system of claim 1, wherein said storage device stores sensor data collected from said furnace, and wherein said computer is further programmed to analyze said sensor data and generate said data markers based upon said analysis of said sensor data.

7. The system of claim 6, wherein said sensor data comprises a plurality of readings collected by one or more auxiliary sensors selected from the following group: an axial encoder, an accelerometer, a roll encoder, a gyroscope, an inertial navigation system, and combinations thereof.

8. The system of claim 1, wherein said computer is further programmed to generate said data markers, and wherein each of said data markers comprises a composite data marker derived from a plurality of individual data markers.

9. The system of claim 8, wherein said computer is programmed to:
- generate said individual data markers;
- normalize said individual data markers; and
- generate said composite data marker by calculating a root mean square of said normalized individual data markers.

10. The system of claim 1, wherein each of said physical features of said furnace is selected from the following group: a bend; an external raised surface; cross-over piping; a thermal well; a weld; a flange; a schedule change; a diameter change; and combinations thereof.

11. A computerized method for displaying inspection data collected from a furnace with a specified physical geometry, wherein said furnace comprises a plurality of tube segments interconnected by a plurality of bends so as to allow stacking of at least a portion of said tube segments, said method comprising:
- partitioning said inspection data at a plurality of data markers each of which identifies a location of a physical feature of said furnace so as to correlate said inspection data to said physical geometry of said furnace;
- generating a display of at least a portion of said partitioned inspection data arranged to represent said physical geometry of a plurality of said tube segments and enable visual detection of a problem area comprising one or more of said tube segments; and
- wherein said inspection data is collected by one or more devices selected from the following group: an ultrasonic transducer, a laser profilometer, and combinations thereof.

12. The computerized method of claim 11, wherein said display is comprised of a two-dimensional or three-dimensional representation of one or more of said stacked tube segments of said furnace.

13. The computerized method of claim 11, further comprising receiving input from a data analyst and generating said data markers based upon said input from said data analyst.

14. The computerized method of claim 11, further comprising analyzing said inspection data and generating said data markers based upon said analysis of said inspection data.

15. The computerized method of claim 14, wherein said inspection data comprises a plurality of readings selected from the following group: wall thickness readings of said furnace, inside radius readings of said furnace, and combinations thereof.

16. The computerized method of claim 15, wherein said inspection data is collected at predetermined time intervals within said furnace.

17. The computerized method of claim 15, wherein said inspection data comprises a plurality of said readings within each of said time intervals.

18. The computerized method of claim 17, wherein each of said data markers is generated by detecting a data clue selected from the following group: an increase in the variation of said wall thickness readings within one of said time intervals, a decrease in the number of said wall thickness readings within one of said time intervals, an increase in the variation of said inside radius readings within one of said time intervals, a decrease in the number of said inside radius readings within one of said time intervals, a change in the centering of said inspection tool, and combinations thereof.

19. The computerized method of claim 11, further comprising analyzing sensor data collected from said furnace and generating said data markers based upon said analysis of said sensor data.

20. The computerized method of claim 19, wherein said sensor data comprises a plurality of readings collected by one or more auxiliary sensors selected from the following group: an axial encoder, an accelerometer, a roll encoder, a gyroscope, an inertial navigation system, and combinations thereof.

21. The computerized method of claim 11, wherein each of said data markers comprises a composite data marker derived from a plurality of individual data markers.

22. The computerized method of claim 21, further comprising:
- generating said individual data markers;
- normalizing said individual data markers; and
- generating said composite data marker by calculating a root mean square of said normalized individual data markers.

23. The computerized method of claim 11, wherein each of said physical features of said furnace is selected from the following group: a bend; an external raised surface; cross-over piping; a thermal well; a weld; a flange; a schedule change; a diameter change; and combinations thereof.

24. A computer-readable medium having computer-executable instructions for performing a method of displaying inspection data collected from a furnace, wherein said furnace comprises a plurality of tube segments interconnected by a plurality of bends so as to allow stacking of at least a portion of said tube segments, said method comprising:
- generating a plurality of data markers each of which identifies a location of a physical feature of said furnace;
- partitioning said inspection data at said data markers so as to correlate said inspection data to an appropriate one of said tube segments of said furnace;
- generating a display of at least a portion of said partitioned inspection data arranged to represent said physical geometry of a plurality of said tube segments and enable visual detection of a problem area comprising one or more of said tube segments; and
- wherein said inspection data is collected by one or more devices selected from the following group: an ultrasonic transducer, a laser profilometer, and combinations thereof.

25. The computer-readable medium of claim 24, wherein said display is comprised of a two-dimensional or three-dimensional representation of one or more of said stacked tube segments of said furnace.

26. The computer-readable medium of claim 24, wherein said method further comprises receiving input from a data analyst and generating said data markers based upon said input from said data analyst.

27. The computer-readable medium of claim 24, wherein said inspection data comprises a plurality of inspection readings selected from the following group: wall thickness readings of said furnace, inside radius readings of said furnace, and combinations thereof.

28. The computer-readable medium of claim 27, wherein sensor data is also collected from said furnace, said sensor data comprising a plurality of sensor readings collected by one or more auxiliary sensors selected from the following group: an axial encoder, an accelerometer, a roll encoder, a gyroscope, an inertial navigation system, and combinations thereof.

29. The computer-readable medium of claim 28, wherein said method further comprises analyzing said inspection data and said sensor data and generating said data markers based upon said analysis of said inspection data and said sensor data.

30. The computer-readable medium of claim 28, wherein each of said data markers comprises a composite data marker derived from a plurality of individual data markers.

31. The computer-readable medium of claim 30, wherein said method further comprises:
generating said individual data markers;
normalizing said individual data markers; and
generating said composite data marker by calculating a root mean square of said normalized individual data markers.

32. The computer-readable medium of claim 24, wherein each of said physical features of said furnace is selected from the following group: a bend; an external raised surface; crossover piping; a thermal well; a weld; a flange; a schedule change; a diameter change; and combinations thereof.

33. A method for displaying inspection data collected from a furnace, said furnace comprising a plurality of tube segments interconnected by a plurality of bends so as to allow stacking of at least a portion of said tube segments, said method comprising:
identifying said bends of said furnace in relation to said inspection data;
partitioning said inspection data at said bends so as to correlate said inspection data to an appropriate one of said tube segments of said furnace;
generating a two-dimensional or three-dimensional representation of at least a portion of said inspection data arranged to represent a physical geometry of a plurality of said tube segments and enable visual detection of a problem area comprising one or more of said tube segments; and
wherein said inspection data is collected by one or more devices selected from the following group: an ultrasonic transducer, a laser profilometer, and combinations thereof.

34. The method of claim 33, wherein said inspection data comprises a plurality of inspection readings selected from the following group: wall thickness readings of said furnace, inside radius readings of said furnace, and combinations thereof.

35. The method of claim 34, wherein sensor data is also collected from said furnace, said sensor data comprising a plurality of sensor readings collected by one or more auxiliary sensors selected from the following group: an axial encoder, an accelerometer, a roll encoder, a gyroscope, an inertial navigation system, and combinations thereof.

36. The method of claim 35, further comprising analyzing said inspection data and said sensor data and identifying said bends based upon said analysis of said inspection data and said sensor data.

37. A method for displaying inspection data collected from a furnace comprising a plurality of tube segments interconnected by a plurality of bends so as to allow stacking of at least a portion of said tube segments, said method comprising:
generating a two-dimensional or three-dimensional representation of said inspection data collected from a plurality of said tube segments of said furnace, said data arranged to represent a physical geometry of said tube segments;
analyzing said two-dimensional or three-dimensional representation and visually detecting a problem area comprising one or more of said tube segments of said furnace; and
wherein said inspection data is collected by one or more devices selected from the following group: an ultrasonic transducer, a laser profilometer, and combinations thereof.

38. The method of claim 37, further comprising correlating said inspection data to an appropriate one of said tube segments of said furnace.

39. The method of claim 37, wherein said inspection data comprises a plurality of inspection readings selected from the following group: wall thickness readings of said furnace, inside radius readings of said furnace, and combinations thereof.

40. A system for displaying inspection data collected from a furnace with a specified physical geometry, wherein said furnace comprises a plurality of tube segments interconnected by a plurality of bends so as to allow stacking of at least a portion of said tube segments, said system comprising:
a storage device for storing said inspection data and sensor data collected from said furnace; and
a computer programmed to:
analyze said sensor data and generate a plurality of data markers based upon said analysis of said sensor data, wherein each of said data markers identifies a location of a physical feature of said furnace so as to correlate said inspection data to said physical geometry of said furnace;
partition said inspection data at said data markers;
generate a display of at least a portion of said partitioned inspection data arranged to represent said physical geometry of a plurality of said tube segments and enable visual detection of a problem area comprising one or more of said tube segments; and
wherein said sensor data comprises a plurality of readings collected by one or more auxiliary sensors selected from the following group: an axial encoder, an accelerometer, a roll encoder, a gyroscope, an inertial navigation system, and combinations thereof.

41. A system for displaying inspection data collected from a furnace with a specified physical geometry, said system comprising:
a storage device for storing said inspection data; and
a computer programmed to:
generate a plurality of individual data markers;
normalize said individual data markers;
generate a composite data marker by calculating a root mean square of said normalized individual data markers;
generate a plurality of data markers each of which comprises a composite data marker;
partition said inspection data at said plurality of data markers each of which identifies a location of a physical feature of said furnace so as to correlate said inspection data to said physical geometry of said furnace; and
generate a display of said partitioned inspection data to thereby enable visual detection of problem areas within said furnace.

* * * * *